United States Patent [19]

D'Aubigne et al.

[11] 4,002,687

[45] Jan. 11, 1977

[54] PROCESS FOR THE HYDROPEROXIDATION OF BRANCHED ALKANES IN A PLURALITY OF STAGES, COMPRISING WASHINGS BETWEEN THE SAID STAGES

[75] Inventors: Jean Merle D'Aubigne, Paris; Jean Maurin, Montivilliers; Joseph Edouard Weisang, Le Havre, all of France

[73] Assignee: Compagnie Francaise de Raffinage, Paris, France

[22] Filed: July 2, 1975

[21] Appl. No.: 592,770

Related U.S. Application Data

[63] Continuation of Ser. No. 407,475, Oct. 18, 1973, abandoned.

[30] Foreign Application Priority Data

Oct. 19, 1972 France .................... 72.37140

[52] U.S. Cl. .................... 260/610 B; 260/610 A
[51] Int. Cl.² .................... C07C 179/02
[58] Field of Search .................... 260/610 B, 610 A

[56] References Cited

UNITED STATES PATENTS

| 2,825,742 | 3/1958 | Schueler et al. ............... 260/610 B |
| 2,862,973 | 12/1958 | Winkler et al. ............... 260/610 B |

FOREIGN PATENTS OR APPLICATIONS

| 1,119,958 | 7/1968 | United Kingdom ........... 260/610 B |

*Primary Examiner*—James O. Thomas, Jr.
*Assistant Examiner*—W. B. Lone
*Attorney, Agent, or Firm*—Curtis, Morris & Safford

[57] ABSTRACT

Process, and resulting product, for improved hydroperoxidation of branched alkanes of at least 4 carbon atoms, especially useful in preparation of isoprene from isopentane; comprising the substantial elimination of acetic acid and similar by-products in the hydroperoxidation reaction which are harmful to the yield of the desired hydroperoxides; all of which is achieved by at least one washing between at least two successive oxidizing reactors. The wash solution may be just water or advantageously a pre-saturated aqueous solution containing the oxidation products which are desired not to be extracted from the organic phase of the reaction medium.

8 Claims, 5 Drawing Figures

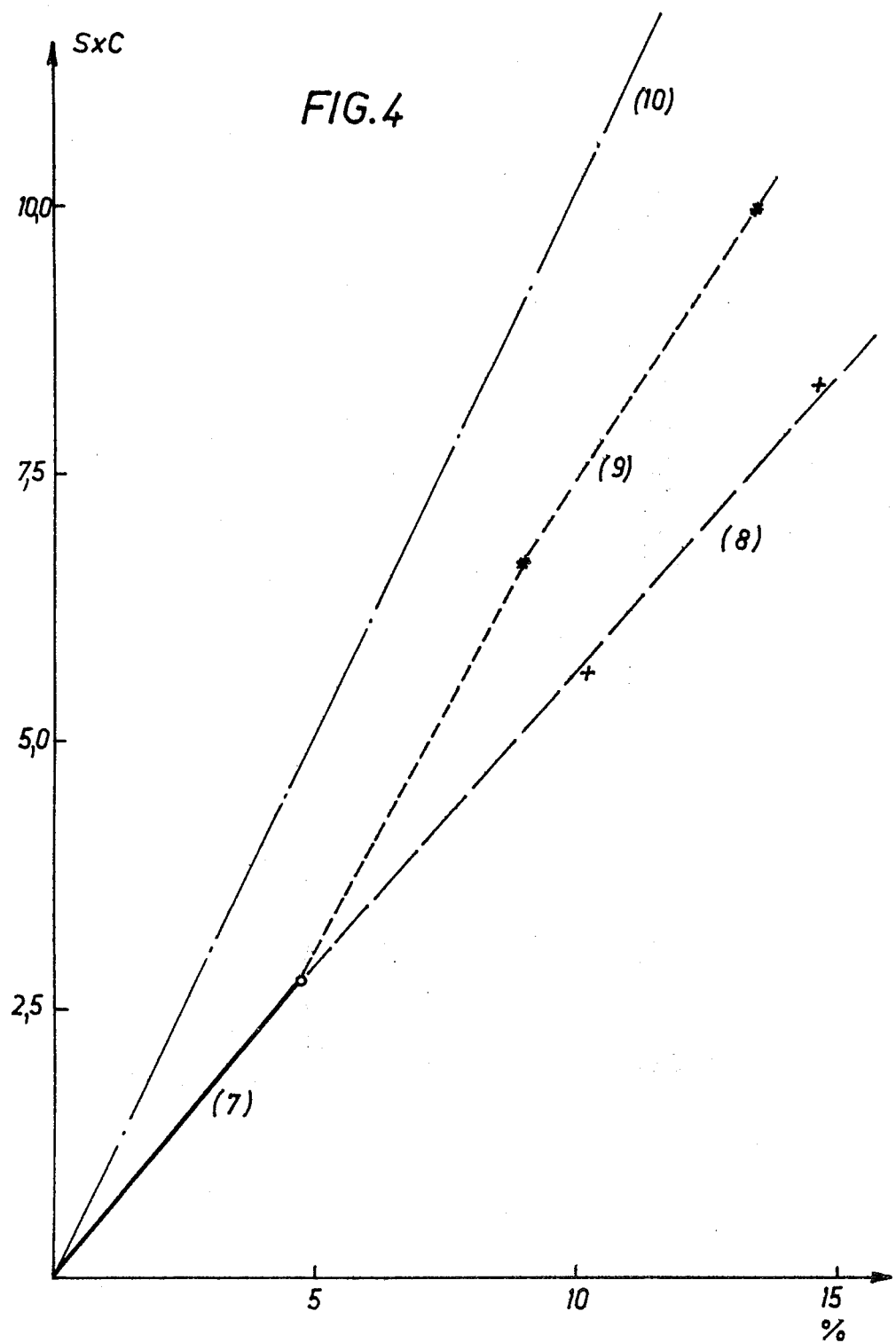

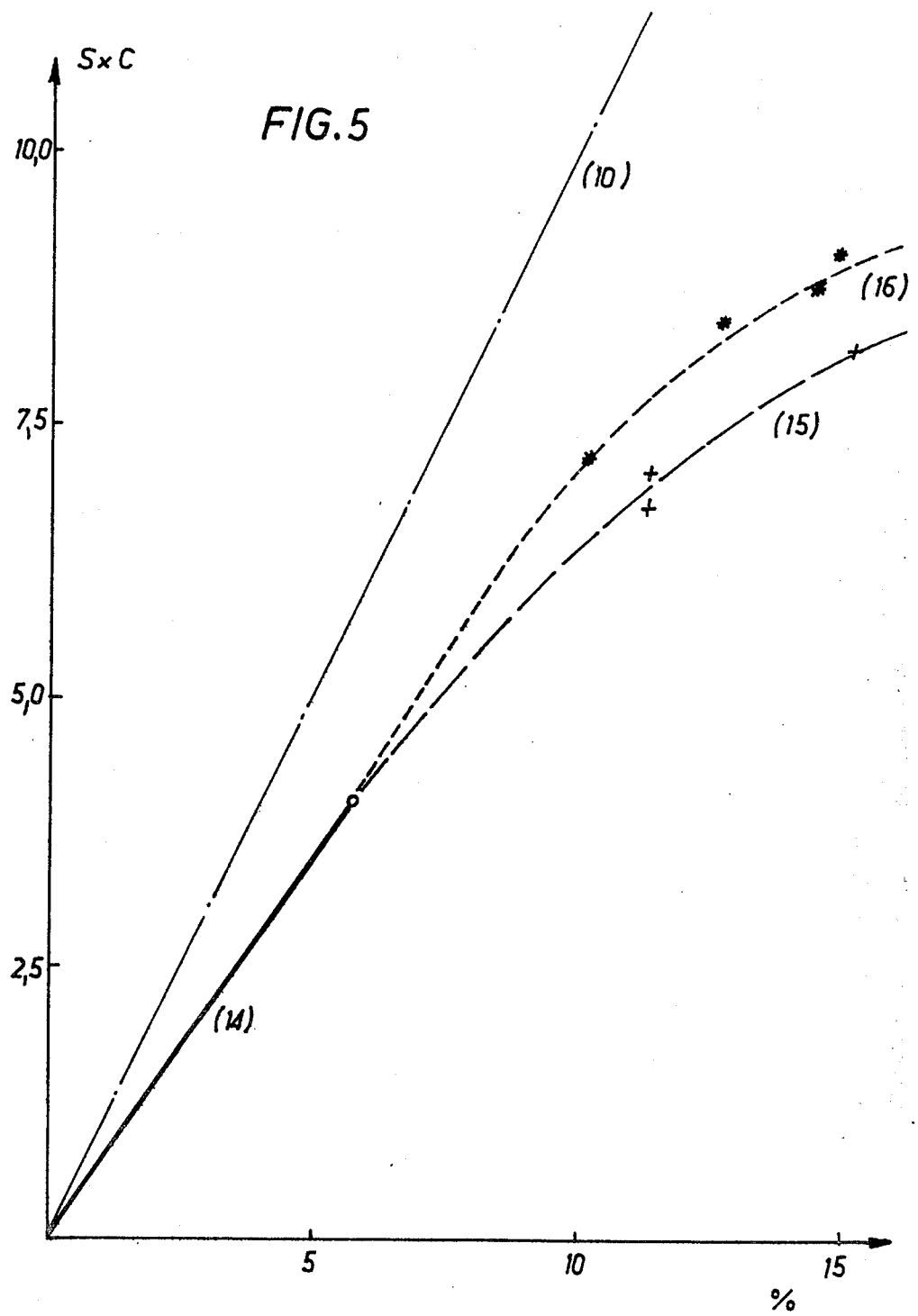

PROCESS FOR THE HYDROPEROXIDATION OF BRANCHED ALKANES IN A PLURALITY OF STAGES, COMPRISING WASHINGS BETWEEN THE SAID STAGES

This is a continuation of application Ser. No. 407,475, filed Oct. 18, 1973 and now abandoned.

The present invention relates to a process for the hydroperoxidation of branched alkanes having a number of carbon atoms greater than or equal to 4, in several stages, comprising a washing with water between at least two of said stages, which process makes it possible to obtain better results than the conventional processes.

In the following description there will be referred to as "hydroperoxide selectivity" or "selectivity" the ratio:

$$\frac{\text{Number of hydroperoxide molecules formed}}{\text{Number of alkane molecules consumed}}$$

and by "conversion" the ratio:

$$\frac{\text{Number of alkane molecules consumed}}{\text{Number of alkane molecules introduced}}$$

Furthermore, the expression "pass", which is well known to the man skilled in the art, will be used to designate a reaction operation which constitutes a part of the overall reaction. Thus a hydroperoxidation reaction is carried out in several "passes", that is to say, in several successive hydroperoxidations.

Finally, a washing may be effected in one or more apparatus customarily serving for such operation, for instance extraction columns or mixer-settler units.

The hydroperoxidation reaction of branched alkanes has been known for a long time. For recent developments in this technology see Ser. No. 127,958; filed Mar. 25, 1971, and the applications therein cited; the subject matter of which applications is incorporated herein by reference. In liquid phase, it leads to the formation, in addition to the hydroperoxides desired, of numerous by-products resulting from various transformations in the reaction medium, particularly the decomposition of the hydroperoxides formed. This reaction is carried out in several stages or passes in several successive reactors arranged in series in order to obtain as high a hydroperoxide selectivity as possible that is to say, close to that which would be obtained in a batch reactor, and an industrially usable conversion of the alkane.

The by-products formed in addition to the desired hydroperoxides are organic compounds of various degrees of oxidation — ketones, alcohols, aldehydes, carboxylic acids. There are also obtained water and hydroperoxides comprising a number of carbon atoms lower than that of the hydrocarbon used, which will be referred to in the course of the description as "light hydroperoxides." In the case of isopentane, the principal products formed which have been identified, in addition to tertiary amyl hydroperoxide, are secondary amyl hydroperoxide, the light hydroperoxides, particularly ethyl and isopropyl hydroperoxides, acetone, 2-methyl 2-butanol and 2-methyl 3-butanol, and acetic acid.

It happens that some of these products, particularly acetic acid favor the decomposition of hydroperoxides, which are already by nature unstable products. The presence of acids is therefore particularly harmful to the yield of the hydroperoxidation reaction, and it is therefore desirable to eliminate these agents which are harmful to the good selectivity of the reaction.

Numerous attempts have therefore been undertaken either to eliminate in particular the acids formed from the reaction medium or to avoid their formation in situ.

Thus French Patent No. 1,506,296 describes the extraction by means of a polar solvent (which is a good solvent for the oxidation products and immiscible with the inital hydrocarbon) of the oxidation products of said hydrocarbon and their purification by washing with an alkaline solution, particularly alkaline carbonate. U.S. Pat. No. 3,445,523 describes the stabilization of hydroperoxides by aqueous solutions of soda, potash or sodium acid phosphate. French Patent No. 1,588,025 moreover describes a treatment of oxidation products of isobutane by a base. Finally, French Patent No. 2,089,819 describes the oxidation of an alkane or cycloalkane in the presence of buffers comprising a basic or amphoteric compound of a metal selected from groups IIA, IIB and IIIB of the periodic system of elements.

Nevertheless, while these processes make it possible to eliminate the harmful agents in whole or in part, they have the drawback of introducing foreign products into the reaction medium or in the phase containing the oxidation products, which foreign products were not present up to then and which it is then necessary to remove from the desired oxidation products.

An object of the present invention is therefore to decrease the quantity of compounds which favor the decomposition of the hydroperoxides, particularly the carboxylic acids, in the phase containing these hydroperoxides, without on the other hand introducing compounds other than those which are already present in the reaction medium.

For this purpose the applicant has developed a new process of hydroperoxidation of branched alkanes having a number of carbon atoms equal to or greater than 4. This process applies particularly well to the hydroperoxidation of isopentane for which the quantity of acid products formed is not neglibible. In addition to the fact that this new process makes it possible to eliminate most of the compounds favoring the decomposition of the hydroperoxides formed (which leads to a gain of selectivity in hydroperoxides for a given rate of conversion of the alkane), the novel washing of the oxidation products leads on the other hand upon a reoxidation to a much better stability of the course of the reaction, particularly for a high rate of conversion.

A preferred embodiment of the present invention is therefore a process for the hydroperoxidation of branched alkanes having a number of carbon atoms greater than or equal to 4. The said process comprises oxidizing the branched alkane in liquid stable by oxygen, whether or not diluted in an inert gas, in successive reactors arranged in series, and is characterized by the fact that one or more washings of the oxidation products with water are effected between at least two reactors.

The extracted phase and the refined phase containing the oxidation products prepared by means of the process in accordance with the invention also constitute embodiments of the invention.

In this specification and the accompanying drawings we have shown and described a preferred embodiment of our invention and have suggested various alternatives and modifications thereof; but it is to be understood that these are not intended to be exhaustive and that many other changes and modifications can be made within the scope of the invention. These suggestions herein are selected and included for purposes of illustration in order that other skilled in the art will more fully understand the invention and the principles thereof and will thus be enabled to modify it and embody it in a variety of forms, each as may be best suited to the conditions of a particular use.

In these drawings:

FIGS. 4 and 5 are curves illustrating the variation of the product of selectivity times conversion as a function of the overall conversion for successive hydroperoxide reactions described in the said examples.

Figure 1:
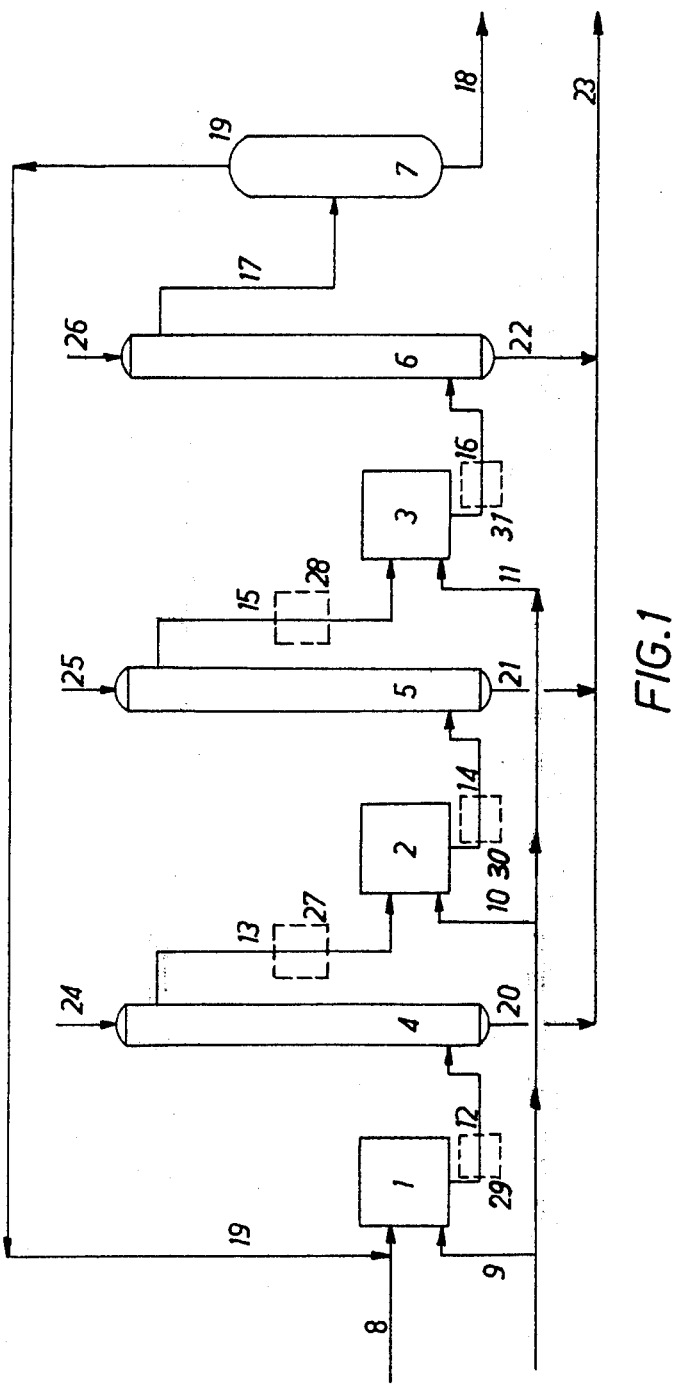
FIG. 1 is a diagram of an installation for carrying out the process of the invention, in the case of the hydroperoxidation of isopentane.

Let use refer first of all to FIG. 1, in which there have been indicated diagrammatically by way of example the different phases of the hydroperoxidation of isopentane by the process in accordance with the invention. In this embodiment, the reaction is carried out in three reactors in series, the oxidation products being subjected to a washing after each pass. In order not to complicate the diagram, the various heat exchangers necessary to adjust the temperatures of the different streams have not been shown. However, nevertheless this is useful.

Into a hydroperoxidation reactor 1 one introduces isopentane through the line 8 and oxygen, diluted or not with an inert gas, through the line 9. The hydroperoxidation reaction is carried out at a temperature generally between 100° and 200° C, as known in the prior art, with vigorous agitation of the medium and under a pressure such that the alkane is in liquid state. A pressure of between 5 and 80 bars is generally used. The oxidation products are withdrawn via the line 12 and feed a wash column 4 in which they are contacted with a wash solution introduced at 24. This solution may be water or an aqueous solution containing oxidation products which it is desired not to extract from the organic phase, for instance hydroperoxides, alcohols, or even possibly ketones. The wash waters are thus pre-saturated so as to extract from the organic phase only a small amount of the products to be refined. The use of a pre-saturated wash water will, however, have to be able selectively to eliminate from it the amount of acid extracted from the oxidation products.

The refined phase is sent by the line 13 into the second oxidation reactor 2 where it undergoes a second hydroperoxidation by oxygen fed through the line 10. The effluxes of the second pass are led via the line 14 into a second wash tower 5 where they are contacted with an extraction agent feeding the wash tower via the line 25. The refined phase evacuated via the line 15 enters into the final reactor 3 where it is oxidized by oxygen fed via 11 into the said reactor. The efflux of the reactor enters the last wash tower via 16 in which tower it is contacted with the extraction agent which enters through 26. The refined phase finally is flashed in the flask 7 which it feeds via the line 17 so as to vaporize the unreacted isopentane which is recycled to the reactor 1 via the line 19. Via line 18 there is thus isolated a phase containing oxidation products comprising hydroperoxides, alcohols, ketones and a small amount of carboxylic acids. Of course, the use of three reactors in series which is described here is not limitative.

The different phases extracted at 20, 21 and 22 from the towers 4, 5 and 6 are combined by the line 23 into a single aqueous solution containing a small amount of hydroperoxides, alcohols, ketones and the largest part of the carboxylic acids formed in the three hydroperoxidation reactors. The recovery and the purification of the different products contained in the aqueous phase can be effected by distillation, azeotropic distillation or any other means known in the art of separation. Thus the small amount of hydroperoxides which is extracted in the aqueous phase can be almost quantitatively recovered by azeotropic distillation, for instance.

The conditions used by the various washings are determined by the following data:

the rate of conversion of the hydrocarbon in the charge to be washed;

the final contents of oxidation products and particularly of acid which it is desired to obtain after washing;

in general one will operate under pressures of 1 to 80 bars and preferably 1 to 40 bars. When the washings are effected at pressures below the pressure prevailing in the reactors located immediately in front of and behind the column it is then necessary to place behind the reactors expanders 29, 30 and 31 and to recompress the refined phases coming from the extraction columns and entering into the reactor following said columns, which can be effected by recirculation pumps shown at 27 and 28. These various pressure adjusting elements which are well known to the man skilled in the art are not necessary when the successive oxidations and the washings are effected under identical pressures.

In order to effect these extractions, one can control the customary parameters which govern the phenomena of transfer of matter but one will more particularly take into account the temperature, the time of stay and the amount of extraction solvent with respect to the charge. The extraction or partition coefficients of the different oxidation products, as a matter of fact, vary very little with the temperature, but in view of the presence of unstable products such as the hydroperoxides in the charge, it will be preferred to limit the range of temperature to an upper limit close to 100° C in order to avoid the thermal decomposition of the hydroperoxides in the wash towers.

In the event that several washings are effected, the respective conditions of each of the washings vary with the conversion rate of the hydrocarbon in the charge to be washed. It is known, as a matter of fact, that all the oxidation products are more or less soluble in water and that moreover the coefficients of extraction vary with the contents of oxidation products in the charge, and therefore with the rate of conversion of the hydrocarbon.

In order to obtain the best overall result, the various passes of the hydroperoxidation can be carried out very close together, as they can use operating conditions and give partial conversion rates which differ from one reactor to the other.

The process in accordance with the invention is therefore very flexible for the user. The examples which follow and which illustrate it in no way limit its scope.

EXAMPLE I

This example is intended to show the effectiveness of a washing with water to eliminate the acids present in the efflux of the first isopentane oxidation pass by oxygen.

The hydrocarbon phase (solvent isopentane) containing the oxidation products is subjected to a washing with water at about 20° C and under a pressure of 1 bar.

Table I sets forth the composition of the charges and of the refined phases, as well as the conversion and selectivity characteristics with respect to the charges coming from a first oxidation pass and solely before washing, for two tests A and B.

This table shows in particular that the washings effected in this way eliminate the greatest part of the acids contained in the charge, as well as about one-half of the compounds with carbonyl function. It will also be noted that a part of the hydroperoxides passes into the extracted phase, but it is relatively easy to recover these products, for instance by simply azeotropic distillation.

There should also be noted in this table the results relating to test B. The contents of hydroperoxide and tertiary amyl alcohol in the refined phase are greater than in the charge. This is due to an evaporation of the solvent, isopentane, during the storage of this phase. The figures giving the contents after washing are therefore higher than they should be, but there should be emphasized the fact that the acid/total hydroperoxides ratio (that is to say, the tertiary amyl and secondary amyl hydroperoxides and light peroxides) which was 0.150/0.584 = 0.257 in the charge has changed after washing to 0.032/0.577 = 0.055, which is an entirely remarkable result and comparable to test A for which this ratio has changed from 0.399 to 0.052.

EXAMPLE II

This example illustrates the washing of a hydrocarbon charge (solvent isopentane) containing the oxidation products with water, with two values of the mass ratio, namely:

water introduced/hydrocarbon phase to be washed

In Table II there are compiled the results of two tests on the same charge which corresponds to a conversion rate of the isopentane of 12.3% in the oxidation preceding this washing.

TABLE II

| | Charge before washing | After washing at 80° C at 30 bars | |
|---|---|---|---|
| | | ratio of water = 7.45 | ratio of water = 20.07 |
| Mass of hydroperoxides | 9.05 | 9.006 | 8.94 |
| Mass of alcohols | 2.60 | 2.47 | 2.33 |
| Mass of carbonyl compounds | 2.81 | 2.58 | 2.30 |
| Mass of acid | 2.08 | 1.07 | 0.60 |

EXAMPLE III

This example illustrates the washing of hydrocarbon charges containing the oxidation products. Several washings were effected on slightly different charges (corresponding to different isopentane conversion rates) and under different conditions of pressure and temperature for tests C, D, E, and identical conditions for tests E, F and G.

Each test leads to the determination of the average distribution coefficients for the different products contained in the charge. This average distribution coefficient for a product A is equal to the ratio:

$$\frac{\text{mass concentration of the product } A \text{ in the extracted phase}}{\text{mass concentration of the product } A \text{ in the refined phase}}$$

In Table III there have been set forth the operating conditions of the washings (temperature, pressure), the rate of conversion of the alkane in the hydrocarbon charge to be washed, and the average coefficients of distribution of the different products.

TABLE III

| TEST | C | D | E | F | G |
|---|---|---|---|---|---|
| Relative pressure, bars | 0 | 8 | 30 | 30 | 30 |
| Temperature, ° C | 25 | 80 | 80 | 80 | 80 |
| Rate of conversion of isopentane | 10.1 | 10.4 | 10.7 | 12.3 | 13.1 |
| | | | Average distribution coefficients | | |
| Acetic acid | 14 | 10.9 | 10.1 | 10.4 | 11.7 |
| Hydroperoxides | 0.8 | 0.07 | 0.06 | 0.06 | 0.03 |
| Tertiary amyl alcohol | 0.4 | 0.1 | 0.2 | 0.2 | 0.1 |
| Compounds with Carbonyl function Acetone | 1.6 | 1.0 | 1.3 | 1.1 | 1.1 |

TABLE I

| | TEST A | TEST B |
|---|---|---|
| Conversion of isopentane | 4.7 | 7.7 |
| Hydroperoxide selectivity | 55 | 57.3 |
| Water ratio volume of water/volume of charge | 0.5 | 0.05 |
| Temperature of washing (° C) | 20 | 20 |
| Pressure of washing (bars) | 1 | .1 |

| Content (in millimols/gram) of the oxidation products | before washing | after washng | before washing | after washing |
|---|---|---|---|---|
| Tertiary amyl hydroperoxide | 0.247 | 0.232 | 0.422 | 0.482 |
| Secondary amyl hydroperoxide | 0.015 | 0.014 | 0.030 | 0.034 |
| Light hydroperoxides | 0.114 | 0.006 | 0.132 | 0.061 |
| Tertiary amyl alcohol | 0.185 | 0.141 | 0.165 | 0.178 |
| Compounds with carbonyl function | 0.268 | 0.140 | 0.414 | 0.280 |
| Acids | 0.150 | 0.013 | 0.150 | 0.032 |

TABLE III-continued

| TEST | C | D | E | F | G |
|---|---|---|---|---|---|
| Methyl isopropyl ketone | — | — | — | — | — |

This table shows that acetic acid has a high coefficient as compared with those of the other oxidized products analyzed.

EXAMPLE IV

This example is intended to illustrate the beneficial effect of a washing of the hydrocarbon phase containing the oxidation products on the further hydroperoxidation reactions.

On the one hand consecutive oxidations are effected without washing between the oxidation reactors and on the other hand the same oxidations are effected, but this time washing the effluxes between the reactors with water under the conditions indicated in Example I.

By way of example there have been compiled in Table IV the results relating to the oxidation in the second pass of the effluxes of the first hydroperoxidation reactor of test B previously described in Example I, on the one hand without subjecting these effluxes to washing and on the other hand by subjecting them to washing with water, the results of which are indicated in Table I. The conditions of the second oxidation were variable and are indicated in Table IV in which "v.v.h." stands for ratio of the hourly flow of liquid phase/volume of the reactor, which is one of the parameters of the oxidation.

Figure 2:
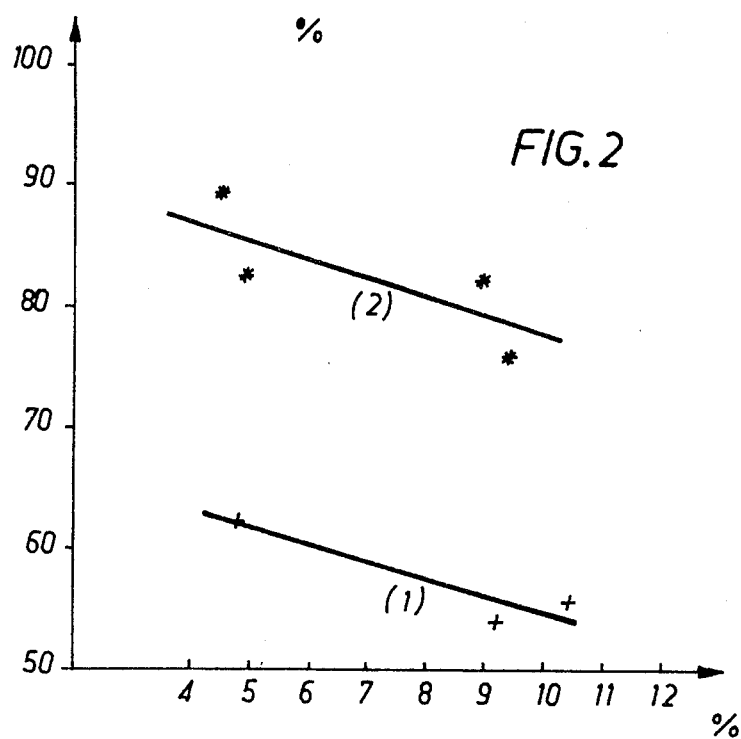
FIGS. 2 and 3 are curves illustrating the variation of the hydroperoxide selectivity as a function of the conversion, in different tests described in the examples which follow.
Figure 3:
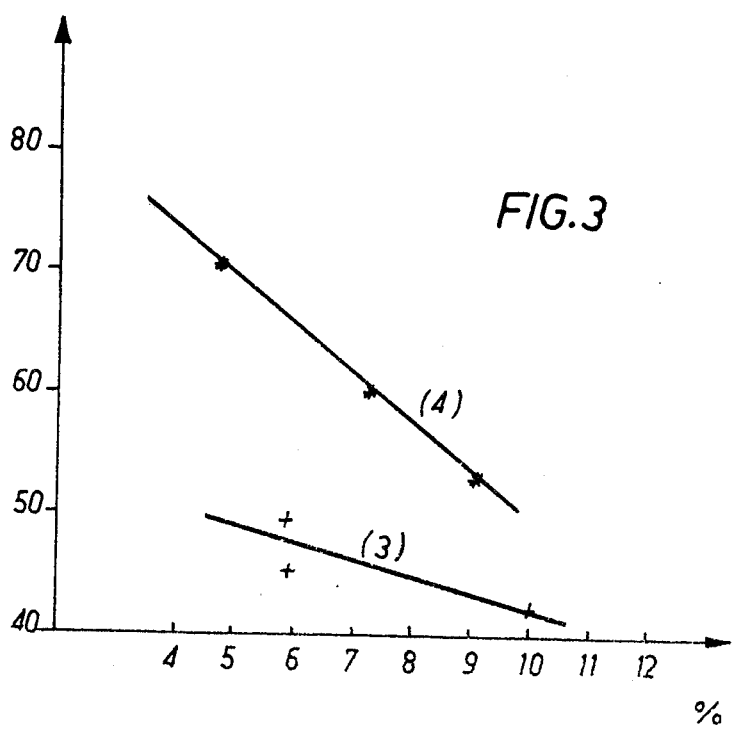

More generally, in FIGS. 2 and 3 there have been shown the curves representing the variation of the hydroperoxide selectivity of the hydroperoxidation reaction as a function of the conversion of said reaction; more particularly there has been shown the partial selectivity of a second oxidation, with or without washing, after the first oxidation. In these figures:

Curves 1 and 3 of FIGS. 2 and 3 thus represent the variation, as a function of the conversion of the second oxidation reaction, of the hydroperoxide selectivity of this second reaction for the unwashed charges of tests A and B of Example I respectively.

Curves 2 and 4 of FIGS. 2 and 3 represent the variations of the same value for the same charges, but this time washed, the composition of which is given in Table I.

Finally, in FIGS. 4 and 5 there is shown the product of selectivity S x conversion C as a function of the overall conversion of two successive hydroperoxidation reactions. This product SxC in fact represents the number of hydroperoxide molecules formed for 100 mols of isopentane introduced, and it is therefore very representative of the results obtained.

TABLE IV

| TEST | Charge used (not washed) B | 1 | 2 | 3 | Charge used in accordance with Example I B | 1 | 2 | 3 |
|---|---|---|---|---|---|---|---|---|
| Temperature | | 146° C | 146° C | 146° C | | 146° C | 146° C | 146° C |
| v.v.h. | | 1.0 | 0.9 | 0.6 | | 0.65 | 0.585 | 0.825 |
| Conversion % | | 5.9 | 5.9 | 10.0 | | 7.3 | 9.1 | 4.7 |
| Selectivity % | | 44.9 | 49.4 | 41.9 | | 60.0 | 54.2 | 70.4 |
| Pressure (bars) | | 31 | 31 | 31 | | 31 | 31 | 31 |
| Rate of flow of oxygen (liter/hr) | | 29.4 | 32.7 | 36 | | 26 | 31 | 29 |
| CONTENTS (millimols/g) | | | | | | | | |
| Hydroperoxides | 0.584 | 0.309 | 0.344 | 0.483 | 0.577 | 0.517 | 0.582 | 0.391 |
| Tertiary amyl alcohol | 0.165 | 0.180 | 0.189 | 0.278 | 0.178 | 0.197 | 0.313 | 0.129 |
| Carbonyl compounds | 0.414 | 0.250 | 0.237 | 0.511 | 0.280 | 0.280 | 0.354 | 0.112 |
| Acids | 0.150 | 0.185 | 0.171 | 0.271 | 0.032 | 0.182 | 0.243 | 0.089 |
| Water | 0.194 | 0.367 | 0.072 | 0.384 | 0.139 | 0.172 | 0.316 | 0.08 |

FIGS. 4 and 5 give the results relating to two tests A and B, some of the stages of which have been previously described.

FIG. 4 relates to test A. In this figure there is shown a curve which is divided into three distinct portions:

One portion 7 representing the value of the product S × C as a function of the conversion of the first oxidation pass.

One portion 8 representing the variation of S × C as a function of the overall conversion at the end of the second oxidation pass, no washing having been effected between the two successive oxidations.

Finally, a portion 9 representing the variation of S × S as a function of the overall conversion at the end of the second oxidation pass when a washing such as described in Example I is effected between the first oxidation and the second.

The same is true of FIG. 5 relating to test B of Example I in which there can be noted the curved portions 14, 15, 16, respectively.

In the two FIGS. 4 and 5 there has also been shown by way of reference the straight line 10 representing the variation of the product SC as a function of the conversion C when S is equal to 100%, which corresponds to the ideal case.

These curves taken together are particularly probative. It is noted, as a matter of fact, that upon an oxidation carried out on a reactor efflux which has been subjected to washing, there is a substantial gain of hydroperoxide, of close to 10%.

The hydroperoxides, extracted by the water at the same time as the acids, are recoverable. The applicants have found that by azeotropic distillation of the wash waters, and therefore of the extracted phase, they could recover about 80 to 90% of the hydroperoxides present in this phase. These recovered hydroperoxides are then subsequently mixed with the oxidation products emerging from the hydroperoxidation unit. This recovery of the hydroperoxides makes it possible to avoid reducing the very beneficial effect of the washing.

We claim:

1. In a process for the hydroperoxidation is isopentane or isobutane, which comprises oxidizing with oxygen said isopentane or isobutane in the liquid state, at a temperature of 100° C to 200° C under a pressure of 5 to 80 bars, by successive passes in successive reactors arranged in series, the improvement comprising the step of washing the oxidation products at a temperature of between 15° C to 100° C, under a pressure of 1 to 80 bars, between at least two oxidizing reactions, by an extraction agent chosen from the group consisting of water and an aqueous solution presaturated with the oxidation products from said process from which the acetic acid reaction product has been substantially removed.

2. A process according to claim 1, wherein all of the carboxylic acid products have been substantially removed.

3. A process according to claim 1, wherein the extraction agent is the aqueous solution efflux from previous washings from which said acid products have been removed by distillation and the other oxidation products have been recirculated.

4. A process according to claim 2, wherein the aqueous solution further has had the ketones of said oxidation products substantially removed prior to use as the extraction agent.

5. A process according to claim 4, wherein the washing is carried out under a pressure of between 1 to 40 bars.

6. A process according to claim 1, wherein the hydroperoxidation reactions and the washing are carried out under the same conditions of pressure.

7. A process for the hydroperoxidation of isopentane according to claim 1, wherein said extraction agent is an aqueous solution saturated with hydroperoxides, acetone, 2-methyl-2-butanol, and 2-methyl-3-butanol.

8. A process according to claim 2, wherein the extraction agent is water.

* * * * *